(12) United States Patent
Lewis et al.

(10) Patent No.: US 6,265,603 B1
(45) Date of Patent: Jul. 24, 2001

(54) INHIBITORS OF ISOPRENYL TRANSFERASE

(75) Inventors: Michael D. Lewis, Andover; Ana Maria Garcia, Belmont; James J. Kowalczyk; Hu Yang, both of Andover; Eric Schwartz, Wakefield, all of MA (US)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/269,915

(22) PCT Filed: Feb. 27, 1998

(86) PCT No.: PCT/US98/04047

§ 371 Date: Apr. 1, 1999

§ 102(e) Date: Apr. 1, 1988

(87) PCT Pub. No.: WO98/38162

PCT Pub. Date: Sep. 3, 1998

Related U.S. Application Data

(60) Provisional application No. 60/040,495, filed on Feb. 27, 1997.

(51) Int. Cl.$^7$ ................................................. C07C 321/00

(52) U.S. Cl. ................................... 560/9; 560/10; 560/16; 562/426; 562/427; 549/493

(58) Field of Search .................................... 560/9, 10, 16; 562/426, 427; 549/493

(56) References Cited

U.S. PATENT DOCUMENTS 5,602,098   2/1997   Sebti et al. .

FOREIGN PATENT DOCUMENTS 95 25086   9/1995   (WO) .
95 34535   12/1995   (WO) .

*Primary Examiner*—Samuel Barts

(57) ABSTRACT

Peptidomimetic isoprenyl transferase inhibitors R6SCHR1'CHR1WCHR2YC(:X)NR3CHR5COR4 wherein R1=OH, H, alkyl, amino group or R1 and R6 together form a heterocyclic ring; R1'=H, alkyl, aryl; R2=H, alkyl, arylalkyl, heteroarylalkyl; R3=H, alkyl, arylalkyl; R4=OH, alkoxy, amino group; R5=natural amino acid residue or D—E—F, where D is alkyl or alkenyl, E is O, S, N, or null, F is H, alkyl, aryl, carboxy amino, etc.; R6=H, alkyl, acyl, etc.; W=alkyl, alkenyl; X=O, S, Y is M—O—P, where M is C0–6 alkyl, O is oxygen-C0–4 alkyl, P is(un)substituted C6–20 aryl are disclosed.

10 Claims, 1 Drawing Sheet

INHIBITORS OF ISOPRENYL TRANSFERASE

CROSS-REFERENCE TO RELATED APPLICATIONS

This application claims priority under 35 U.S.C. §119 based upon U.S. Provisional Application Ser. No. 60/040,495 filed Feb. 27, 1997, the entire disclosure of which is hereby incorporated by reference.

BACKGROUND OF THE INVENTION

This invention concerns peptidomimetic isoprenyl transferase inhibitor compounds useful in the treatment of human cancers.

Ras oncogenes are prevalent in over 20% of all human cancers. The compounds of the invention inhibit the post-translational processing of ras proteins, thereby inhibiting ras protein function.

Ras proteins are present in all cell types, and are thought to take part in normal cellular signal transduction mechanisms. Ras mutations are thought to cause hyperproliferation of cells; mutated ras genes are known as oncogenes. In particular, ras oncogenes are found in approximately 30% of all lung cancer, 30% of all myeloid leukemia, 50% of all colorectal carcinoma, and 90% of all pancreatic carcinoma. Barbacid, M., *Ann. Rev. Biochem.*, 56:779 (1987), Bos, J. L., *Cancer Res.* 49:4682 (1989). Examples of ras mutations include H-ras, K-ras, and N-ras.

Like other members of the superfamily of small GTP-hydrolyzing proteins, ras-encoded proteins, both normal and mutated, require post-translational processing for cell membrane association and biological activity. Maltese, W. A., *FASEB Journal*, 4:3319 (1990), Hancock, J. F. et al., *Cell*, 57:1167 (1989).

The post-translational processing of ras proteins is signaled by a short carboxyl-terminus consensus sequence, known as the CAAX box. This sequence signals which of two isoprenyl groups, farnesyl or geranylgeranyl, is to be attached to ras proteins by cellular enzymes. A farnesyl group is a 15 carbon isoprenyl group, while a geranylgeranyl group is a 20 carbon isoprenyl group. Isoprenyl groups are multimers of isoprene, a 5 carbon compound. For farnesylated proteins, such as ras, lamin B, and γ-transducin, C is cysteine, A is an aliphatic amino acid, and X (the carboxyl-terminal amino acid) is methionine, serine, or glutamine. Geranylgeranylated proteins such as Rap, Rho and other small GTP-binding proteins, have similar CAAX sequences in which X is usually leucine, or occasionally is phenylalanine. In vivo, ras proteins are preferentially farnesylated.

Post-translational processing of the ras-encoded protein includes at least three steps. First, reaction with farnesyl pyrophosphate attaches a farnesyl group to the Cys residue on the sulfhydryl side chain. Second, a specific protease cleaves the three carboxy-terminal amino acids. Third, the carboxylic acid moiety of the now-terminal cysteine is methylated to a methyl ester. The farnesyl transferase enzyme (FTase) mediates the attachment of the farnesyl group to a protein. The geranylgeranyl transferase I enzyme (GGTase I) mediates the attachment of the geranylgeranyl group to a protein. Post-translational processing, particularly farnesylation, of ras proteins is critical for in vivo ras protein function. Among other things, farnesylation of ras oncogene products is known to be essential for ras-induced cellular transformation. Cox, A. D. and Der, C. A. Critical Rev. in Oncogenesis, 3 (4) 365–400 (1992). Upstream of FTase, farnesylation of a ras protein can be inhibited by mevalonate synthesis inhibitors such as lovastatin or compactin, which are HMG-CoA reductase inhibitors. Direct inhibition of FTase by short peptides or peptide-like substrates has also been demonstrated. Since ras proteins mediate the transformation of normal cells to cancer cells in many human cancers, compounds which inhibit prenylation will, therefore, inhibit the growth of ras-related cancers.

SUMMARY OF THE INVENTION

This invention is directed to novel peptidomimetic isoprenyl transferase inhibitor compound useful in the treatment of ras-associated human cancers. Ras-associate a human cancers are those in which a mutated form of the ras gene product are commonly found, e.g., lung cancers, myeloid leukemia, colorectal carcinoma, pancreatic carcinoma, and the like.

The invention concerns the compounds themselves, the preparation of these compounds, and the in vitro and in vivo isoprenyl transferase activity of these compounds. Another aspect of the invention is directed to the clinical use of the compounds to decrease isoprenyl transferase activity in biological systems, and to the physiological consequences of inhibition of isoprenyl transferase.

The compounds of the invention possess advantages for pharmaceutical use such as enhanced pharmacological selectivity and efficacy.

The compounds of the invention may be used clinically to treat medical conditions where a decrease in isoprenyl transferase activity is beneficial. The compounds of the invention can be used to inhibit post-translational modification of oncogenic ras proteins by FTase, thereby down-regulating ras protein-stimulated cell proliferation. Accordingly, the invention is directed to the treatment of various forms of ras-associated cancer. Some compounds of the invention inhibit post-translational modification of ras proteins by the related GGTase I, which also results in down-regulation of ras protein function. Certain compounds of the invention are selective or specific for FTase and are preferred over compounds which are selective for GGTase I.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

DEFINITIONS

In accordance with the present invention and as used herein, the following terms are defined with the following meanings, unless explicitly stated otherwise.

The term "aryl" refers to aromatic groups which have at least one ring having a conjugated pi electron system and includes carbocyclic aryl, heterocyclic aryl and biaryl groups, all of which may be optionally substituted.

Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen. Heterocyclic aryl groups include furanyl, thienyl, pyridyl, pyrrolyl, N-lower alkyl pyrrolo, pyrimidyl, pyrazinyl, imidazolyl, oxazolyl, thiazolyl, isooxazolyl, and the like, all of which may be optionally substituted.

Carbocyclic aryl groups are groups wherein the ring atoms of the aromatic ring are carbon atoms. Carbocyclic aryl groups include monocyclic carbocyclic aryl groups and optionally substituted naphthyl groups.

The term "optionally substituted" means the substitution on aryl groups, whether carbocyclic, heterocyclic, or biaryl, with one to four substituents, the substituents being independently selected from lower alkyl, hydroxy, lower alkoxy, lower alkanoyloxy, halogen, carboxy, carboxyalkyl, cyano, nitro, trihalomethyl, amino, lower alkylamino, lower acylamino or lower alkoxycarbonyl.

The term "aralkyl" refers to an alkyl group substituted with an aryl group. Suitable aralkyl groups include benzyl, picolyl, and the like. The aryl group of an aralkyl moiety may be optionally substituted. Aralkyl groups may be described herein as ($C_{x-y}$ aryl)($C_{a-b}$ alkyl) where "x-y" denotes the range of the number of carbon atoms in the aryl moiety of the aralkyl group and "a-b" denotes the range of the number of carbon atoms in the alkyl moiety of the aralkyl group.

The term "lower" when used herein in connection with organic radicals or compounds respectively, defines them as comprising up to and including 10, preferably up to and including 6 and preferably one or two carbon atoms. Such organic radicals or compounds may have straight chain or branched chain structures.

The terms (a) "alkylamino", (b) "arylamino", and (c) "aralkylamino", respectively, refer to the groups —$NR_1R_2$ where each of $R_1$ and $R_2$ is independently hydrogen, alkyl, or aryl.

The term "carboxamide" or "carboxamido" refers to —$CONR_2$ where each R is independently hydrogen or aryl, alkyl.

The term "alkyl" refers to saturated aliphatic groups including straight-chain, branched chain and cyclic groups.

The term "alkenyl" refers to unsaturated groups which contain at least one carbon-carbon double bond and includes straight-chain, branched-chain and cyclic groups.

The term "alkynyl" refers to unsaturated groups which contain at least one carbon-carbon triple bond and includes straight-chain, branched-chain and cyclic groups.

The term "prodrug" as used herein refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein. The groups illustrated are exemplary, not exhaustive and one skilled in the art could prepare other known varieties of prodrugs. Such prodrugs of the compounds of Formula 1, fall within the scope of the present invention.

The term "pharmaceutically acceptable salt" includes salts of compounds of Formula 1 derived from the combination of a compound of this invention and an organic or inorganic acid. The compounds of Formula 1 are useful in both free base and salt form. In practice the use of salt form amounts to-use of base form; both forms are within the scope of the present invention.

The term "treatment" includes prophylactic or therapeutic administration of the invention, for the cure or amelioration of disease or symptoms associated with disease, and includes any benefits obtained or derived from the administration of the described compounds.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer.

DETAILED DESCRIPTION OF THE INVENTION

Figure 1:
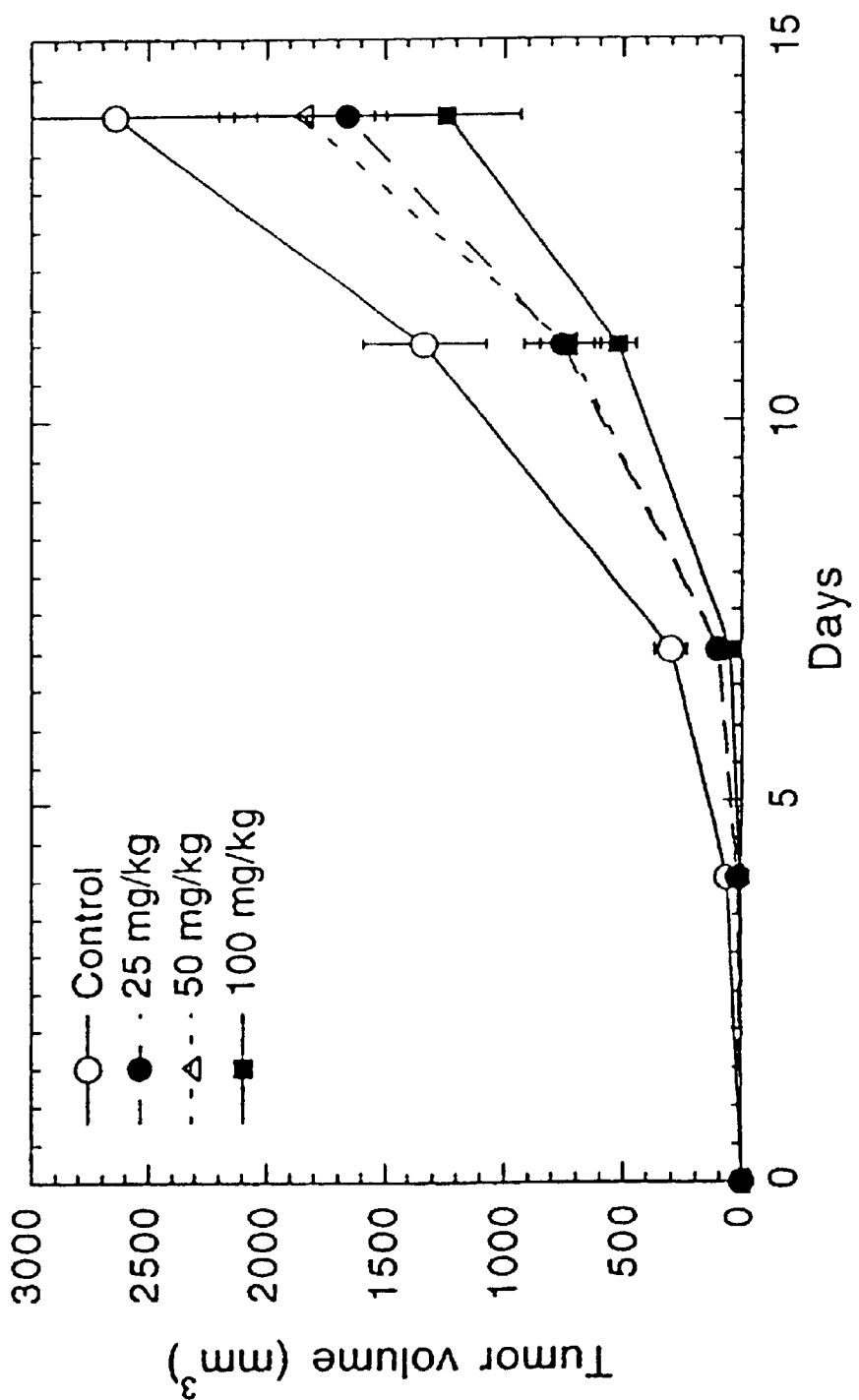
FIG. 1 shows inhibition of tumor growth in mice treated with vehicle or with compound 1.

All patents, patent applications and references referred to in this specification are hereby incorporated by reference in their entirety. In case of a conflict between material incorporated by reference and the present specification, the present specification controls.

In one aspect, the present invention relates to the use of substituted peptidomimetics which comprise compounds of the general Formula 1 and their use,

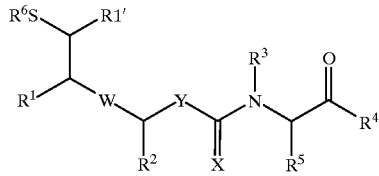

Formula 1 where:
$R^1$ is hydroxy, hydrogen, $C_{1-8}$alkyl or $NR^7R^8$ wherein $R^7$ and $R^8$ are independently hydrogen, $C_{1-8}$ alkyl, $C_{1-8}$ acyl, $C_{2-14}$ alkyloxycarbonyl or when taken with $R^6$ forms a heterocyclic ring containing from 3 to 10 carbon atoms;

$R^{1'}$ is hydrogen, lower alkyl or lower aryl;

$R^2$ is hydrogen, $C_{1-8}$ alkyl, ($C_{6-40}$ aryl)($C_{0-6}$ alkyl), or ($C_{3-10}$heteroaryl) ($C_{0-6}$ alkyl);

$R^3$ is hydrogen, $C_{1-6}$ alkyl, ($C_{6-20}$ aryl)($C_{0-6}$ alkyl);

$R^4$ is hydroxy, $C_{1-6}$ alkoxy, or $NR^{11}R^{12}$ where $R^{11}$ and $R^{12}$ are independently hydrogen, $C_{1-8}$ alkyl, $C_{6-18}$aryl, $C_{4-18}$heteroaryl, $C_{1-8}$alkyl-$C_{6-18}$aryl or when taken together $C_{2-8}$heterocycloalkyl;

$R^5$ is the residue of a natural amino acid or is D—E—F where D is $C_{1-12}$ alkyl or $C_{2-12}$ alkenyl, E is oxygen, sulfur, nitrogen or null and F is hydrogen, $C_{1-10}$ alkyl, $C_{6-12}$aryl, $CO_2R^9$, $NR^9R^{10}$ or $C(O)N\ R^9R^{10}$ where $R^9$ and $R^{10}$ are independently hydrogen, $C_{1-8}$ alkyl or when taken together $C_{2-8}$heterocycloalkyl;

$R^6$ is hydrogen, $C_{1-8}$ alkyl, $C_{1-8}$ acyl or when taken together with $R^1$ forms a heterocyclic ring containing from 3 to 10 carbon atoms;

W is $C_{0-8}$ alkyl, or $C_{2-8}$ alkenyl;

X is oxygen, sulfur or two hydrogen atoms;

Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;

and pharmaceutically acceptable salts thereof.

In general, preferred are compounds where:
$R^1$ is $NR^7R^8$ wherein $R^7$ and $R^8$ are independently hydrogen or $C_{1-8}$ alkyl;
$R^{1'}$ is hydrogen or $C_{1-5}$ alkyl;
$R^2$ is hydrogen or $C_{1-8}$ alkyl;
$R^3$ is hydrogen or $C_{1-6}$ alkyl;
$R^4$ is hydroxy or $C_{1-6}$ alkoxy;
$R^5$ is D—E—F where D is $C_{1-12}$ alkyl or $C_{2-12}$ alkenyl, E is oxygen, sulfur, or null and F is hydrogen, $C_{1-10}$ alkyl, $N^R9R^{10}$ or $C(O)N$ $R^9R^{10}$ where $R^9$ and $R^{10}$ are independently hydrogen, $C_{1-8}$ alkyl or when taken together $C_{2-8}$heterocycloalkyl;
$R^6$ is hydrogen, $C_{1-8}$ alkyl, $C_{1-8}$ acyl or when taken together with R1 forms a heterocyclic ring containing from 3 to 10 carbon atoms;
W is $C_{0-8}$ alkyl, or $C_{2-8}$ alkenyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

More preferred are compounds where:
$R^1$ is $NR^7R^8$ wherein $R^7$ and $R^8$ are independently hydrogen or C1–8 alkyl;
$R^{1'}$ is hydrogen or $C_{1-3}$ alkyl;
$R^2$ is hydrogen or $C_{1-8}$ alkyl;
$R^3$ is hydrogen or $C_{1-6}$ alkyl;
$R^4$ is hydroxy or $C_{1-6}$ alkoxy;
$R^5$ is D—E—F where D is $C_{1-12}$ alkyl or $C_{2-12}$ alkenyl, E is sulfur or oxygen and F is hydrogen, $C_{1-10}$ alkyl or $NR^9R^{10}$ where $R^9$ and $R^{10}$ are independently hydrogen, $C_{1-8}$ alkyl or when taken together $C_{2-8}$heterocycloalkyl;
$R^6$ is hydrogen, $C_{1-8}$ alkyl, $C_{1-8}$ acyl or when taken together with $R^1$ forms a heterocyclic ring containing from 3 to 10 carbon atoms;
W is $C_{0-8}$ alkyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

And most preferred are compounds where
$R^1$ is $NR^7R^8$ wherein $R^7$ and $R^8$ are hydrogen;
$R^{1'}$ is hydrogen or methyl;
$R^2$ is hydrogen or $C_{1-4}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is hydrogen or $C_{1-3}$ alkyl;
$R^6$ is hydrogen;
W is $C_{0-3}$ alkyl;
X is oxygen or two hydrogen atoms;
Y is —M—O—P— where M is $C_{0-6}$ alkyl, O is oxygen-$C_{0-4}$ alkyl and P is $C_{6-2}0$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

Also included within the scope of the present invention are compounds of Formula 1 as described above wherein $R^6$ is the moiety

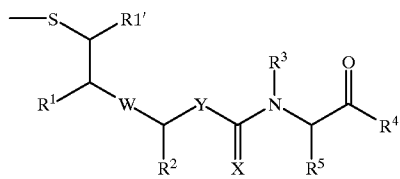

wherein $R^1$, $R^{1'}$, $R^2$, $R^3$, $R^4$, $R^5$, W, X and Y are selected such that the compounds are disulfide bond-linked dimers.

Also preferred are compounds wherein $R^4$ is hydroxy or $C_{1-6}$ alkoxy, i.e. compounds which are either carboxylic acids (from which water soluble salts are easily prepared) and lower alkoxy esters (which in some cases may facilitate cell wall penetration of the drug).

Preparation of the Compounds of the Invention

Another aspect of this invention is directed to processes for preparing compounds of Formula I. Disclosed herein are general synthetic routes for preparing the compounds of this invention. A representative synthesis of a compound of this invention, compound 1, is shown below.

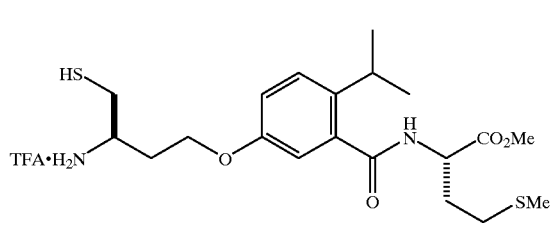

The reagents and starting materials are well known to those skilled in the art. Certain reagents and starting materials for the synthesis of the compounds of the invention for this preparation are described in detail by Lewis, et al., in U.S. application Ser. No. 07/935,050, the disclosure of which is hereby incorporated by reference.

The synthesis proceeds by the preparation of two "portions" of the target molecule which are then coupled together. The abbreviations used in the synthetic schemes below are well-known in the art, are further elaborated in the Examples and can be found in standard organic chemistry journals and texts.

Although following synthetic route describes the preparation of compound 1, use of alternate starting materials will yield other analogs of this invention. Thus the synthesis is general and representative in nature. For example, use of differently substituted aromatic rings in the preparation of the "right side" of the molecule will produce different analogs.

The preparation of the "left side" of the molecule for the preparation of compound 1 is outlined below. The additional details for the preparation of some of the compounds are described in Lewis, et al., in U.S. application Ser. No. 07/935,050.

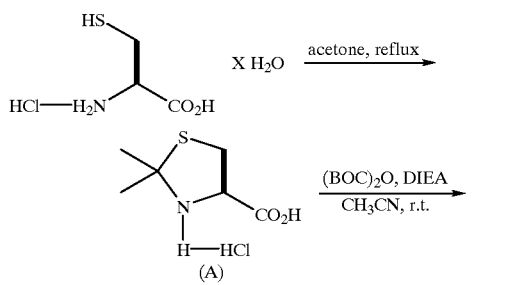
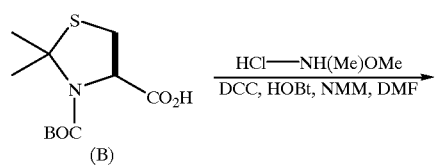
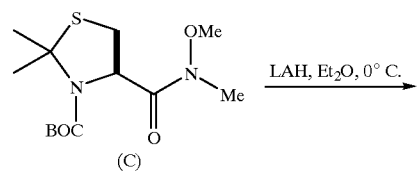
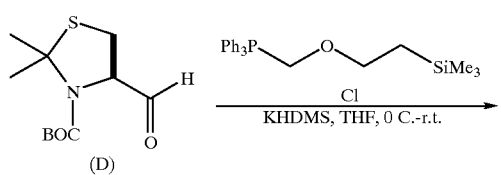
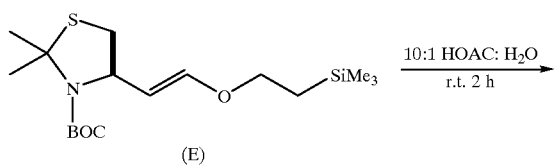
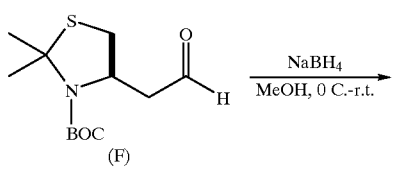
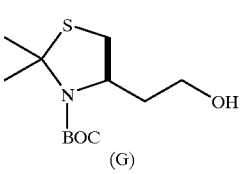
The "right side" may be synthesized by the route shown below:
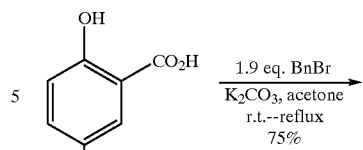
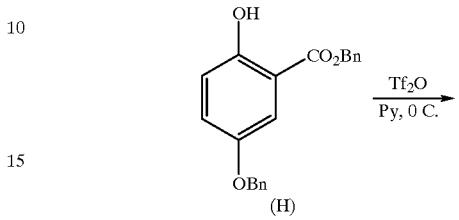
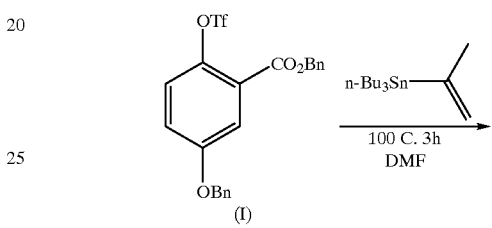
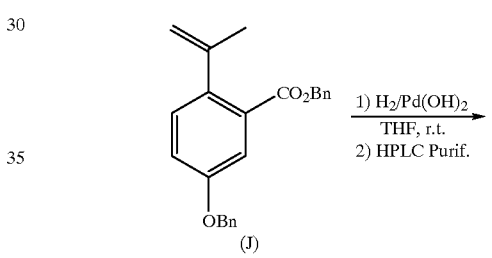
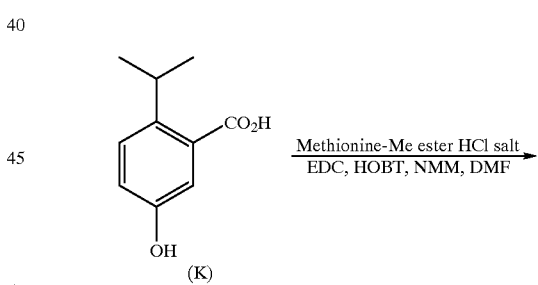
The two halves are coupled together and the appropriate protecting groups removed to give the desired compound as illustrated below:
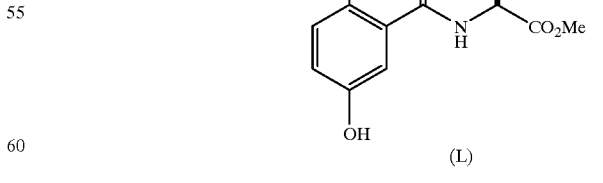

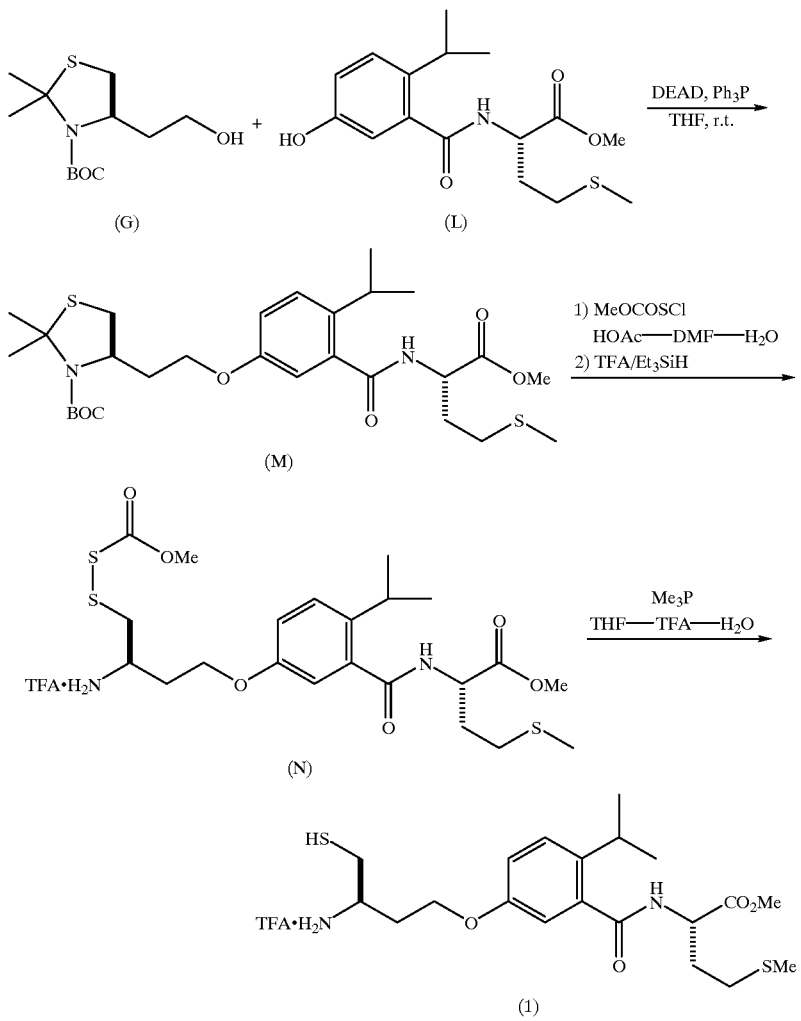

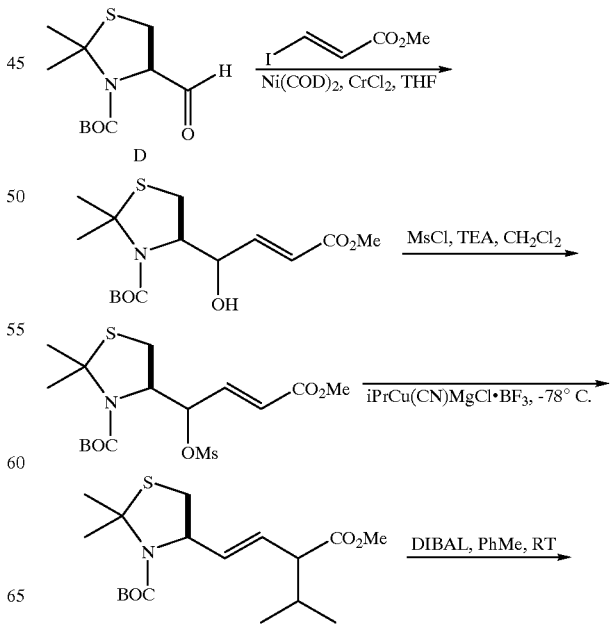

The synthetic route shown above, modified by methods well-known in the art, provides versatile pathways to the compounds of this invention as provided in the Examples. Use of different amino acids in the preparation of the "left side" of the molecule will result in compounds which have varying substitution patterns. The general synthesis outlined herein can be used to extend and modify the carbon chain which is generated from the carboxyl group of the starting amino acid, and provide an appropriate alcohol to couple the "left" side to the "right side." Most preferred are compounds which are made from amino acids of the L configuration.

Modifications of the synthetic route shown above would be within the skill of the art. For example, use of compound O (also described by in Lewis, et al., in U.S. application Ser. No. 07/935,050) as an intermediate in the synthesis of the "left side" of a compound of the invention, using the chemistry outlined above, will provide compound 2 of the invention. As one skilled in the art will appreciate, use of organometallic reagents which comprise other organic radicals in the scheme outlined below will provide other analogs within the scope of the present invention. Furthermore other alcohols as the "left side" would also provide other analogs of this invention.

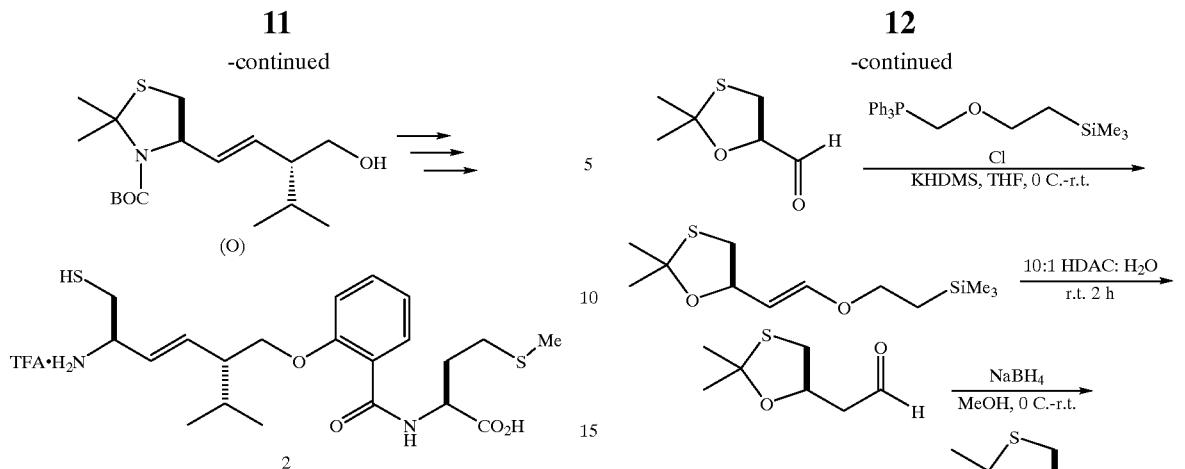

Similarly, use of differently substituted aromatic carboxylic acids in the preparation of the "right side" will result in analogs with differing substitutent patterns around the aromatic ring. The use of different amino acids in the preparation of the "right side" will provide analogs with different amino acid substituents. For example, use of 3-hydroxy-2-naphthanoic acid (commercially available, for instance from Aldrich Chemical Company, Milwaukee, Wis.) as the starting material will provide compound 3. Most preferred are analogs which are made from aromatic carboxylic acid starting materials in which the alcohol and the carboxylic acid moieties are separated by 5 or fewer carbon atoms.

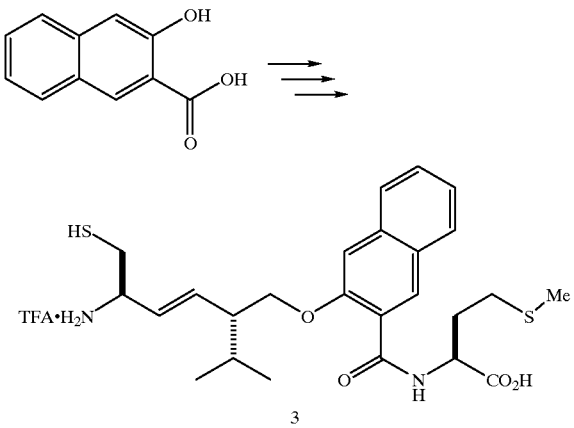

For analogs with oxygen at position $R^1$, the appropriate starting materials may be made as follows. The 3-thio-2-hydroxypropanoic acid starting material may be prepared by the methods described in U.S. Pat. No. 2,828,208.

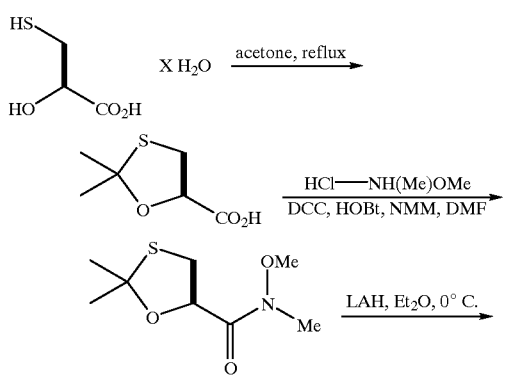

Compounds of the present invention in which $R^1$ is alkyl may be prepared by the following method. Use of different anhydrides (compounds with different "R" substituents) gives different "right side" starting materials and as one well skilled in the art is aware, the number of commercially available anhydrides is extremely large, allowing for the preparation of numerous analogs contained within the present invention.

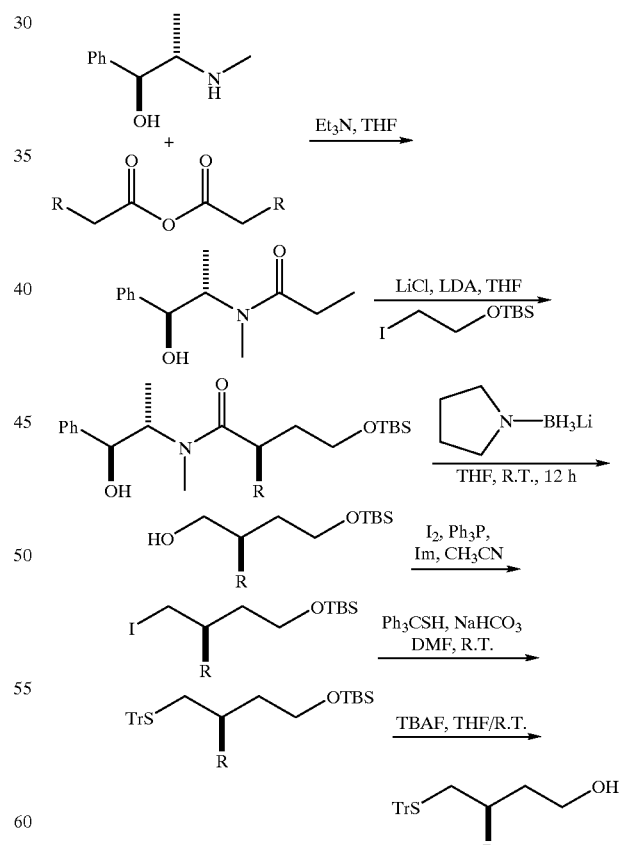

Compounds within the invention in which X is two hydrogen atoms may be prepared as follows starting from the appropriate aromatic carboxylic acid prepared as outlined above.

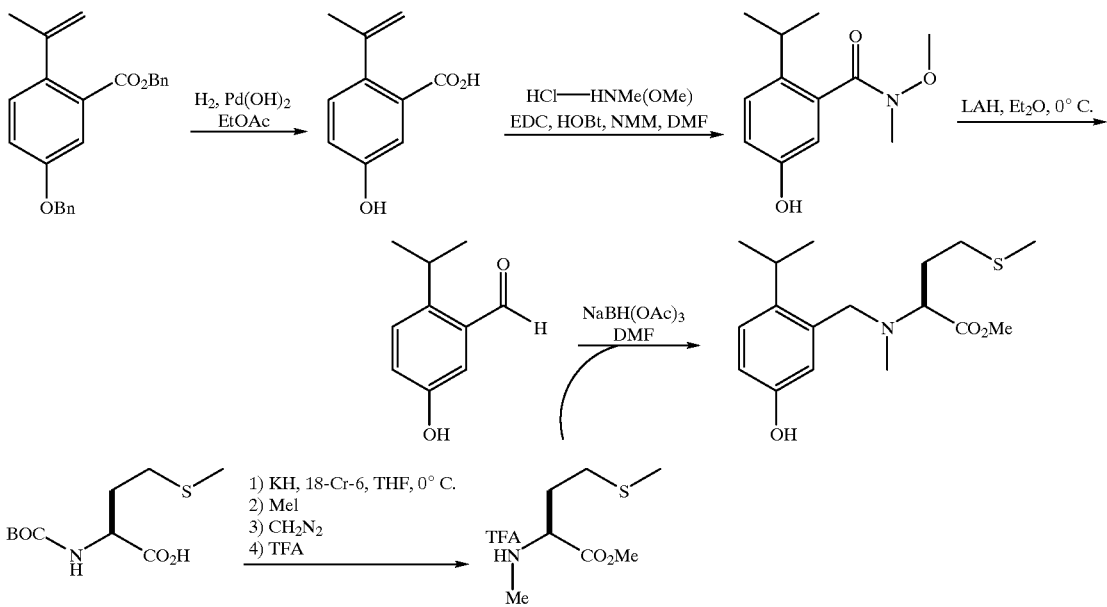
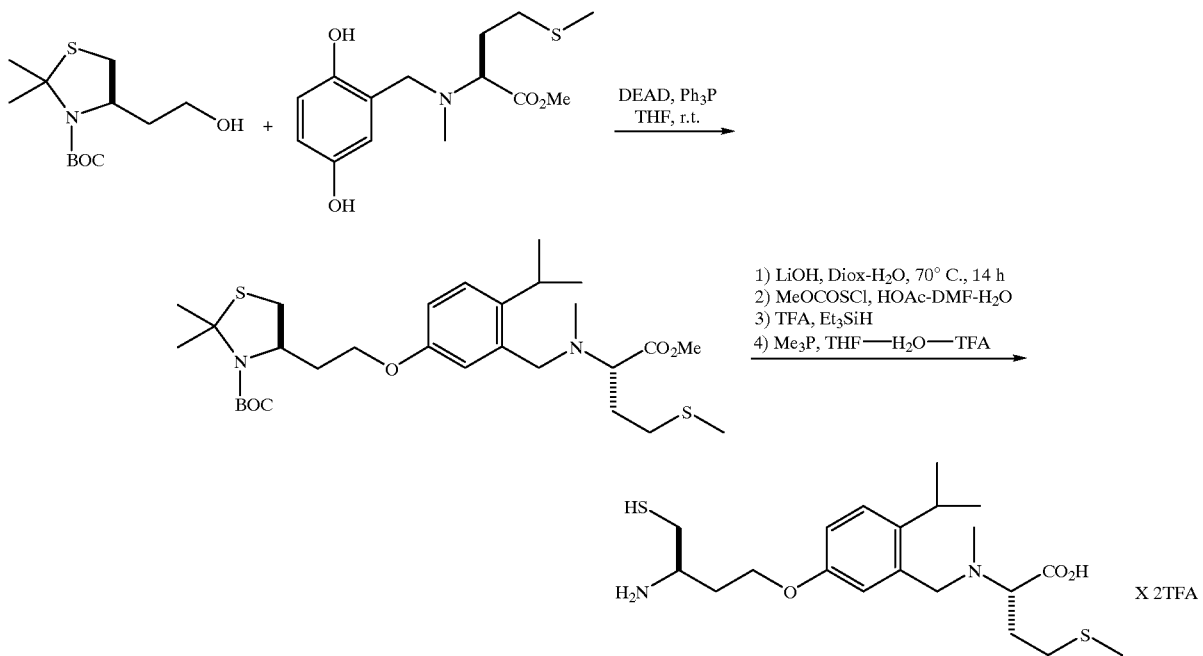
The appropriate "right side" of the molecule, once synthesized according to the scheme above, it is coupled with an alcohol which is prepared as previously described. The "left side" alcohol and the "right side" are coupled as shown below.
If the ester is desired, the following synthetic pathway may be followed.

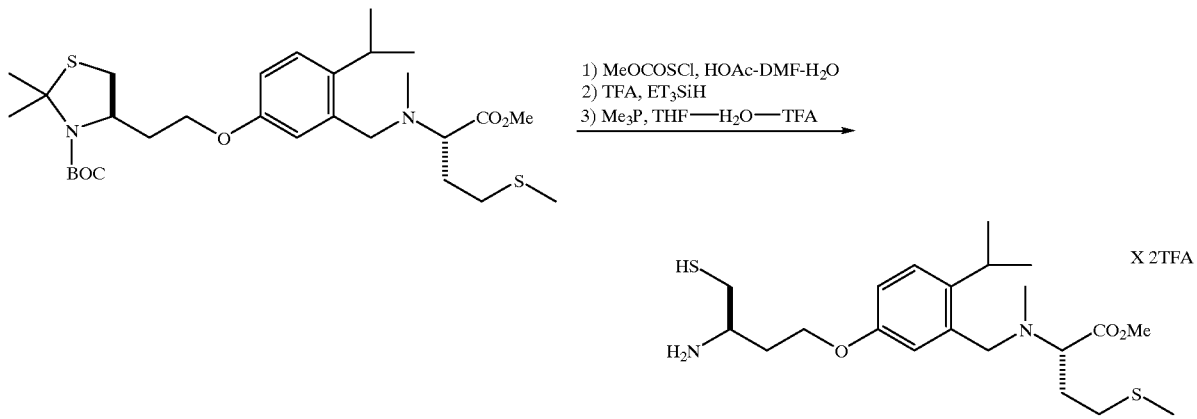

Dimer compounds of the present invention may be prepared as follows. The activated disulfide, compound N, is treated with a solution of the appropriate thiol, in this case compound 1. The mixture was stirred for 14 hours at room temperature and then chromatrographed to give the desired disulfide dimer. Other dimers may be prepared in a similar manner.

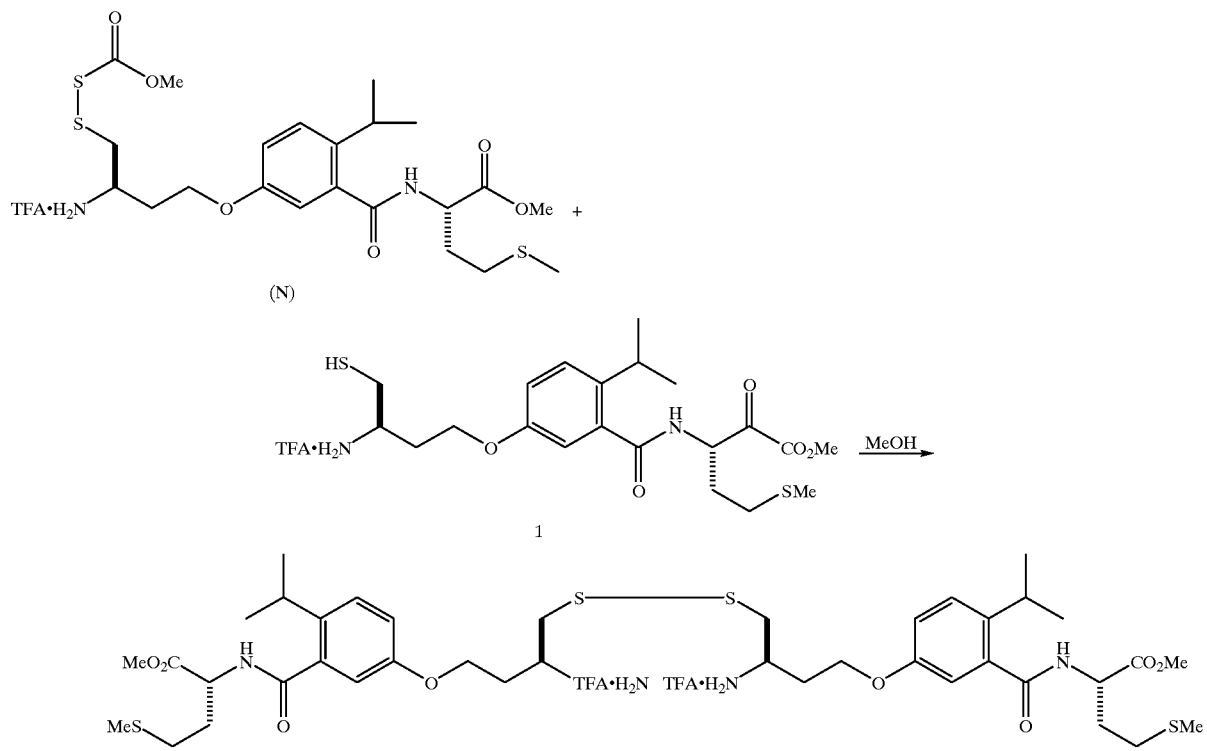

Similarly, compounds with a slightly different right half may be prepared as outlined below.

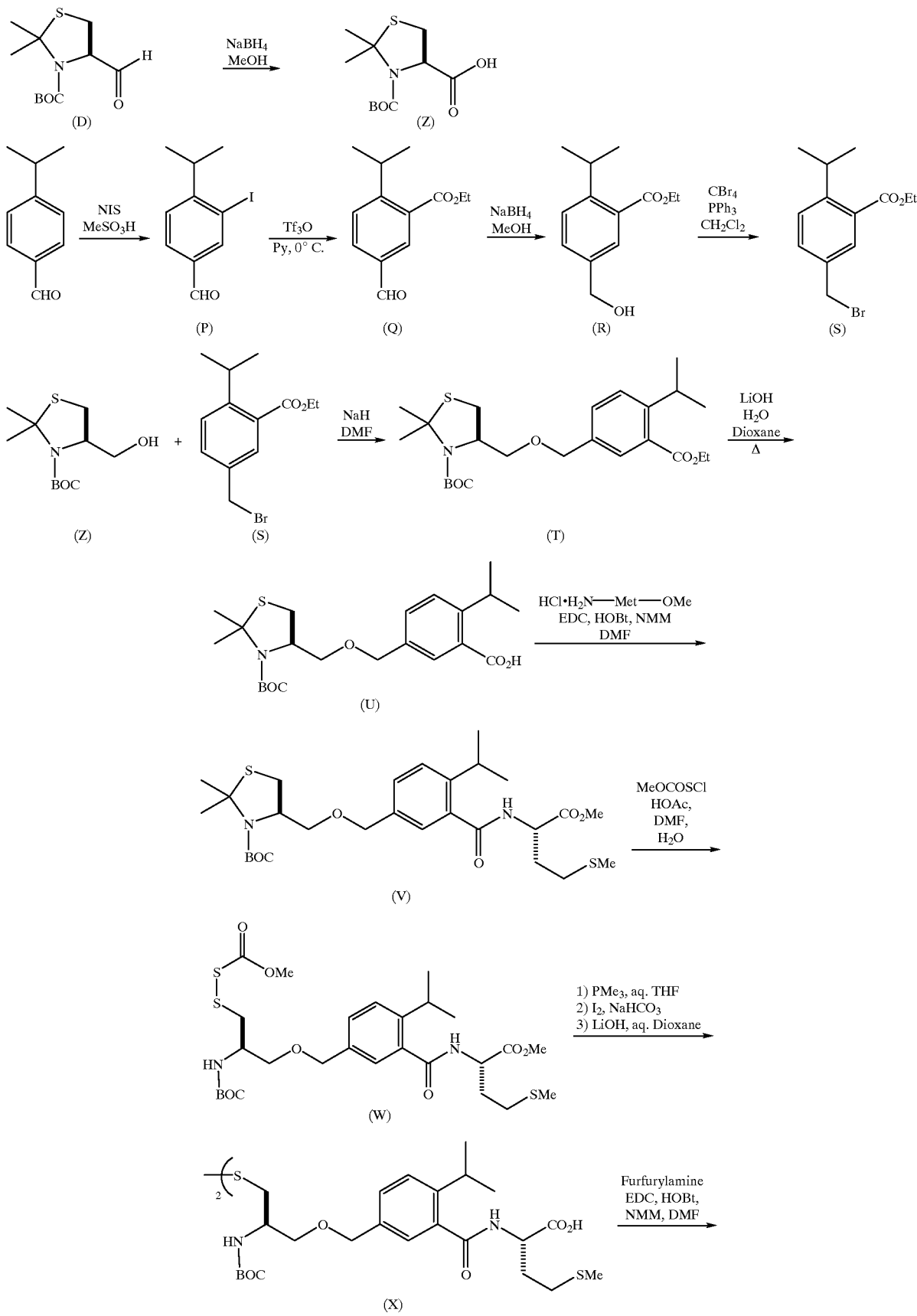

-continued
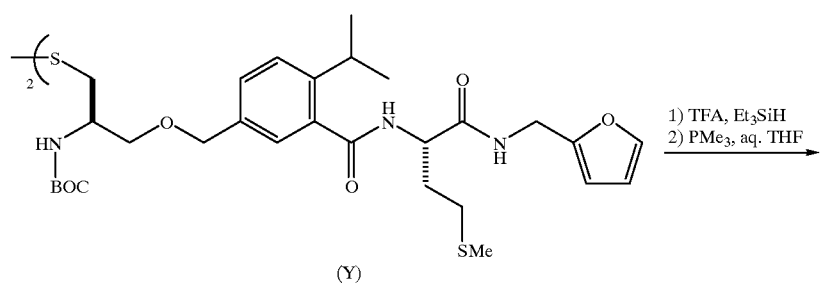
(Y)
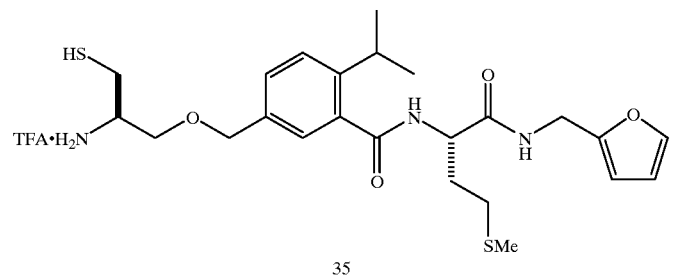
35
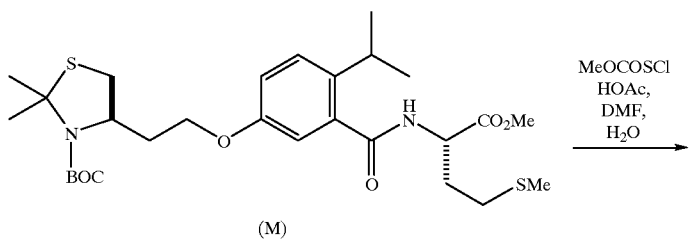
(M)
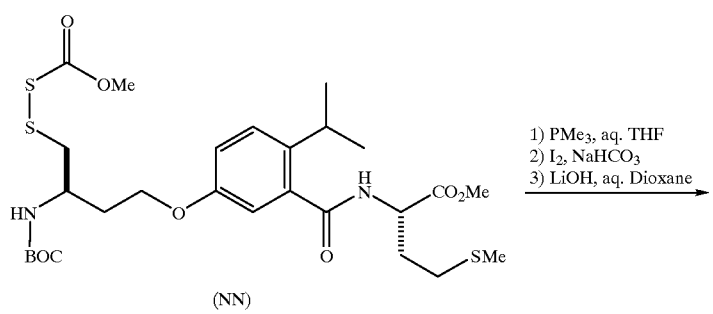
(NN)
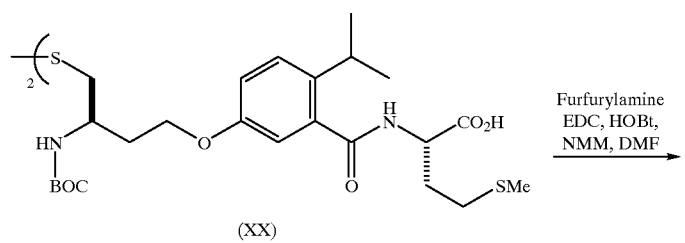
(XX)
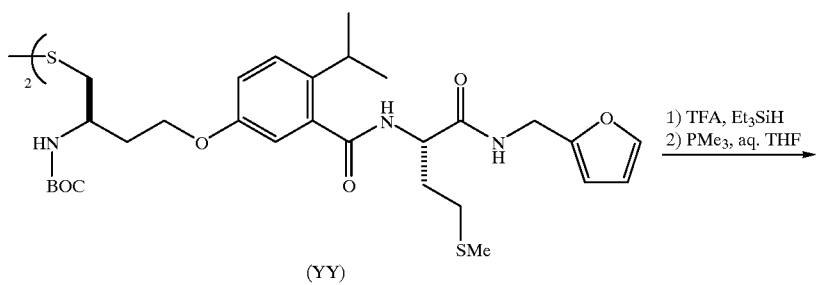
(YY)

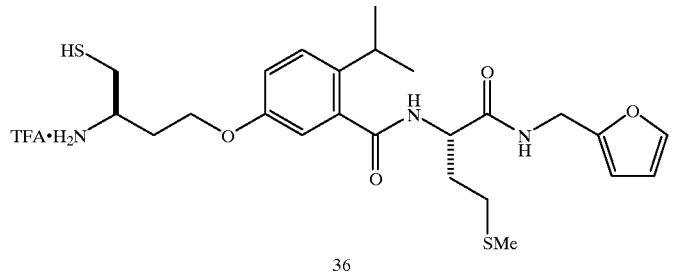

36

FORMULATIONS

Compounds of the present invention are administered to subjects in need of treatment in dosages which are effective to produce inhibition of isoprenyl transferases. Compound 1, the most potent compound of the series, can be administered, for example, by iv infusion of a solution or suspension with a concentration of between about 1 and 10 mg/mL. The total dose per subject per day should be between about 10 and 200 mg/m$^2$, preferably between about 25 and 150 mg/m$^2$, and more preferably between about 50 and 100 mg/m$^2$ of body surface area. A representative dosage regimen is daily administration for 5 days followed by 2 days rest. The administration cycle may be repeated every two weeks. Those of ordinary skill in the art will recognize that modification of dosage and administration routes can be made based on subject responsiveness to treatment.

An alternative method of administration is by way of infusion pump, at about the concentration indicated above.

The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of cancer.

Pharmaceutical compositions containing the active ingredient may be in any form suitable for the intended method of administration.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrroiidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood that the specific dosage form and dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

EXAMPLES

The compounds of this invention and their preparation can be understood further by the examples which illustrate some of the processes by which these compounds are prepared or used. Theses examples do not limit the invention. Variations of the invention, now known or further developed, are considered to fall within the scope of the present invention as hereinafter claimed.

Specific compounds of the present invention are referred to by compound number according to the tables below.

1
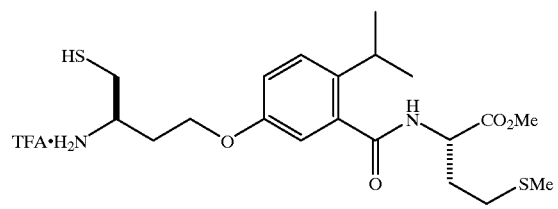
2
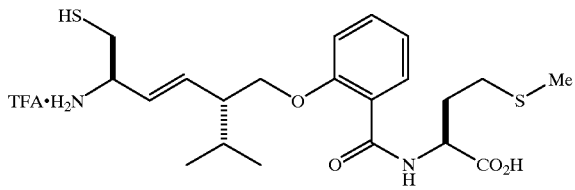
3
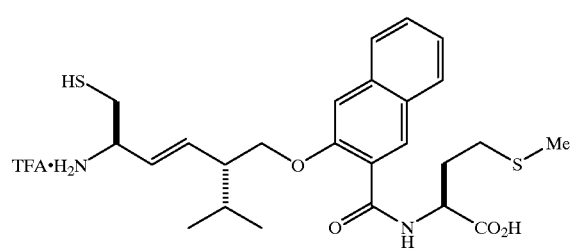
4
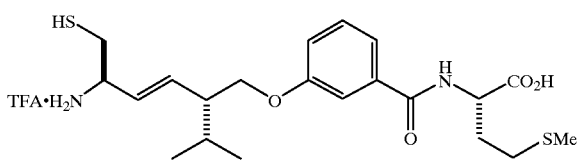
5
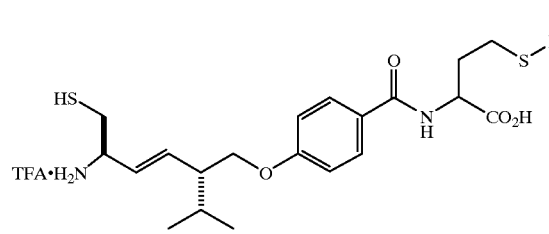
6
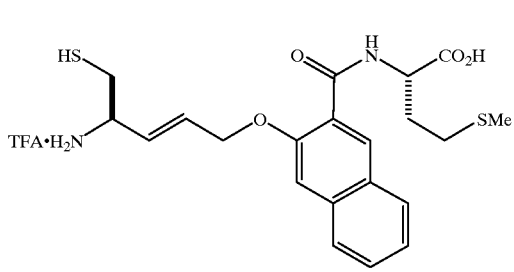
7
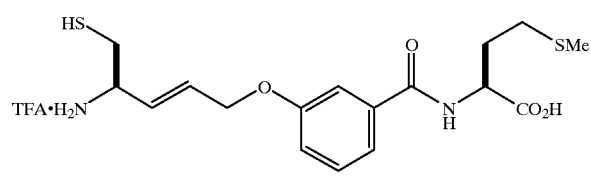
8
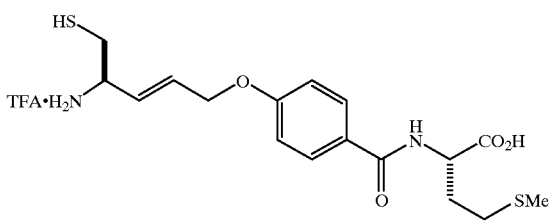
9
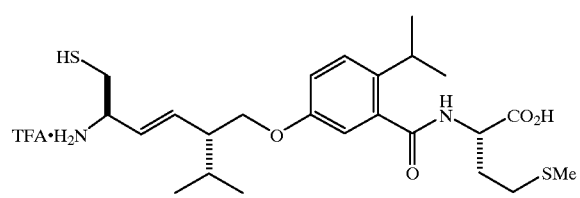
10
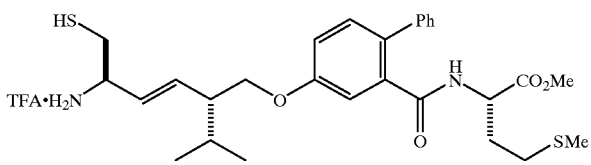
11
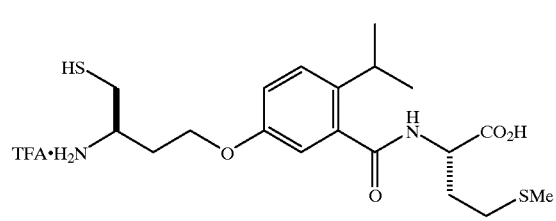
12
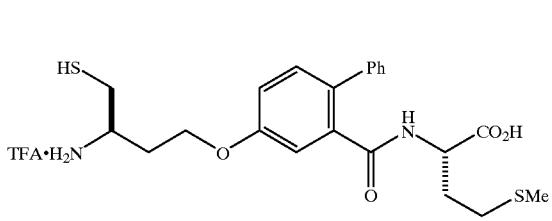

-continued
13
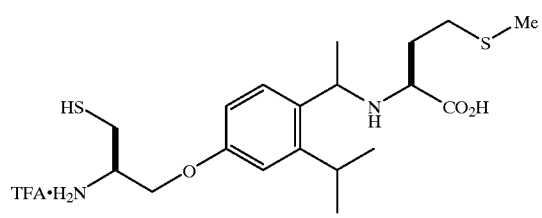
14
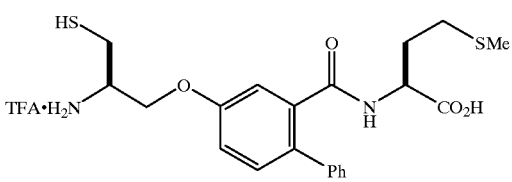
15
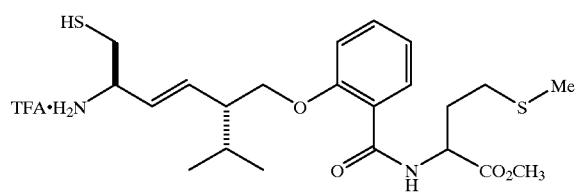
16
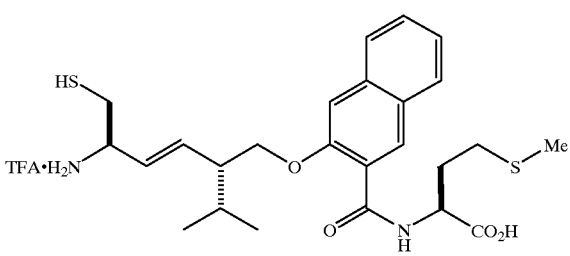
17
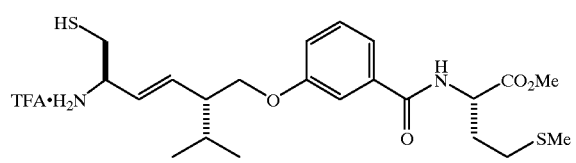
18
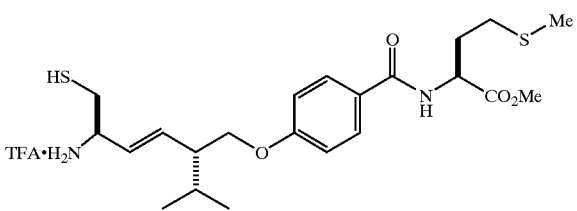
19
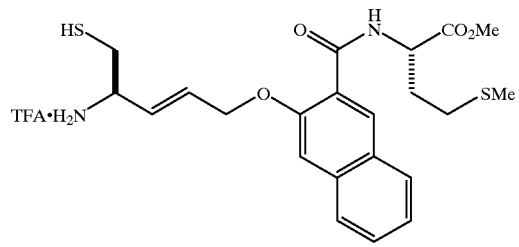
20
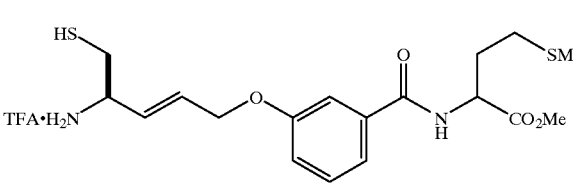
21
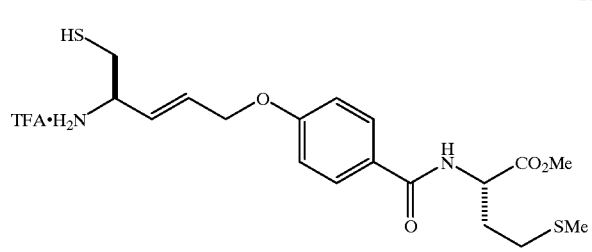
22
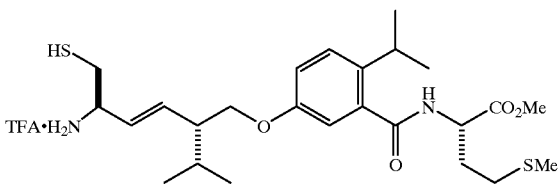
23
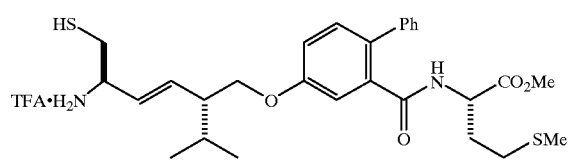
24
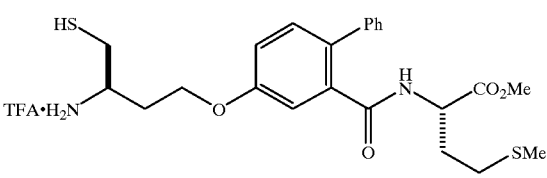

-continued

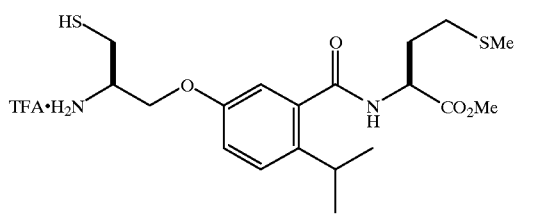
25

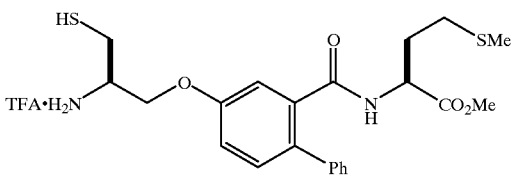
26

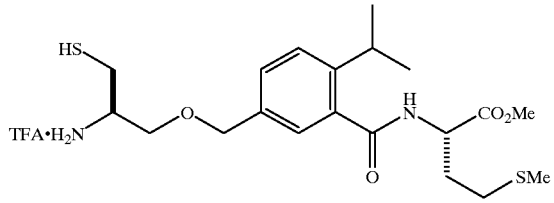
27

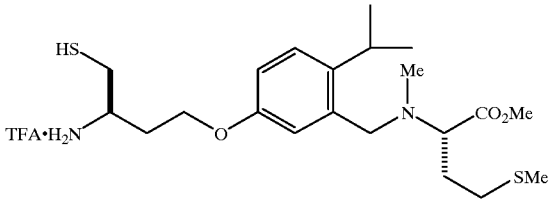
28

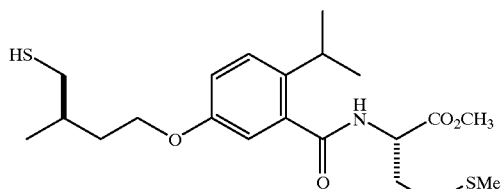
29

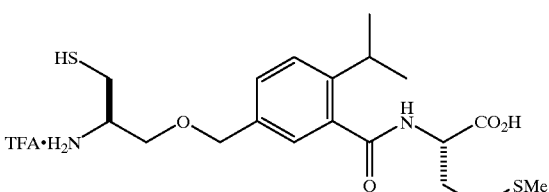
30

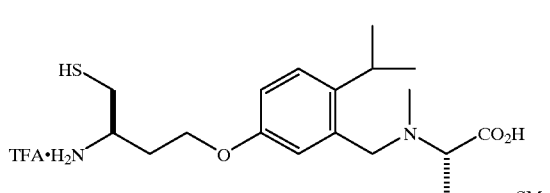
31

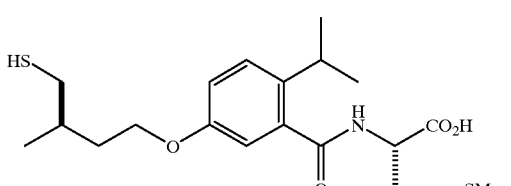
32

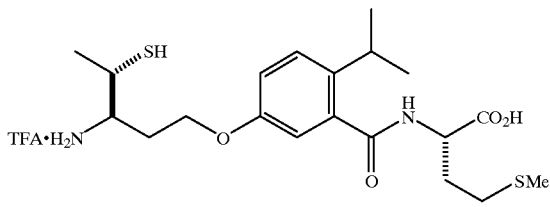
33

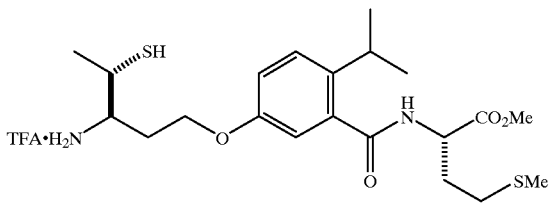
34

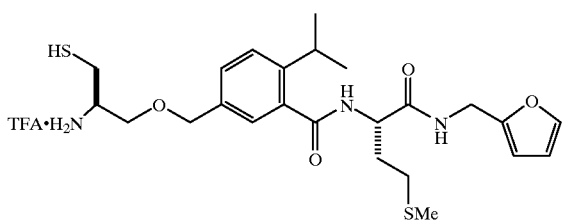
35

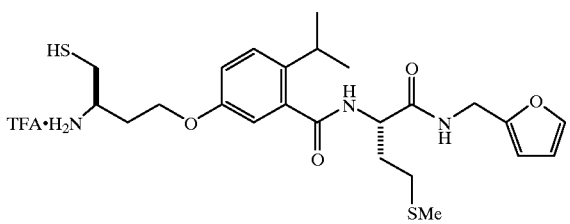
36

Example 1

Preparation of Compound 1 by Route 1

Unless otherwise noted, all sensitive reactions were conducted under an inert atmosphere. Intermediates and final products gave spectral analysis (for example, nuclear magnetic resonance spectroscopy and/or mass spectroscopy) consistent with their proposed structures. Reactions were monitored by silica gel thin layer chromatography. Preparative chromatography, unless otherwise noted, was performed on silica gel.

The process referred to as "drying and chromatography" is performed as follows: upon completion of the reaction by TLC (or other suitable methods of analysis) the final solution is extracted with brine, dried over anhydrous sodium sulfate, the solvent removed under reduced pressure and the residue chromatographed on silica gel using hexanes/ethyl acetate as the eluent. All reactions requiring anhydrous conditions were run under dry nitrogen or argon. All compounds gave proton and carbon NMR spectra consistent with their structure.

The Preparation of Compound 1

Compound E: A 0.5 M toluene solution (7.0 mL, 3.5 mmol) of potassium bis(trimethylsilyl)amide was added dropwise to a THF (20 mL) suspension of [2-(trimethylsilyl)ethoxymethyl]triphenylphosphonium chloride cooled at 0° C. The mixture turned orange-red. The mixture was stirred for 30 min. during which period the reaction was allowed to warm to the room temperature. Then the mixture was cooled to 0° C. and a THF (30 mL) solution of Compound D, prepared by the method of Lewis, et al., in U.S. application Ser. No. 07/935,050, (520 mg, 2.12 mmol) was added. The mixture was stirred at 0° C. for 1 h, during this period the reaction is allowed to warm to the room temperature. The solvent was evaporated under vacuum. The residue was dissolved in ethyl acetate and was extracted by water and brine. Drying and chromatography yielded a colorless oil Compound E (940 mg, >100%).

Compound F: A solution of acetic acid (9 mL) and water (1 mL) containing 5 (572 mg, 1.29 mmol) was stirred at room temperature for 2 h. The solvents were evaporated under vacuum and the residue was dissolved in ethyl acetate and extracted with sodium bicarbonate solution and brine. Final drying and chromatography yielded a colorless oil Compound F (235 mg, 70%).

Compound G: Sodium borohydride was added to a methanol solution (9 mL) of compound F (235 mg, 0.907 mmol) in one portion. The mixture was stirred at room temperature for 0.5 h. The methanol was then evaporated under vacuum and the residue was dissolved in ethyl acetate and extracted by saturated ammonium chloride and brine. Drying and chromatography yielded a white solid (187 mg, 79%).

Compound H: An acetone suspension (100 mL) of 2,5-dihydroxybenzoic acid (555 mg, 3.60 mmol), benzyl bromide (0.813 mL, 6.84 mmol), and potassium carbonate (994 mg, 7.20 mmol) was stirred at room temperature for 12 h and then reflux for 24 h. The reaction was allowed to cool to room temperature. The acetone was evaporated under vacuum. The residue was dissolved in ethyl acetate and extracted by water twice. Drying and chromatography yielded a white solid (898 mg, 75%).

Compound I: Trifluoroacetic anhydride (0.432 mL, 2.57 mmol) was added to a pyridine solution (16 mL) of benzyl 5-benzyloxy-2-hydroxybenzoate, compound H, (572 mg, 1.713 mmol) cooled at ° C. The mixture was stirred at 0–4° C. for 12 h and was diluted with ether (100 mL). The mixture was extracted by water twice and 1N HCl. Drying and chromatography yielded a colorless oil (604 mg, 76%).

Compound J: trans-Benzyl(chloro)bis(triphenylphosphine)palladium(II) (20 mg, 0.026 mmol) was added to a DMF solution (4 mL) of benzyl 5-benzyloxy-2-trifluoroacetoxybenzoate, compound I, (604 mg, 1.30 mmol), lithium chloride (167 mg, 3.90 mmol), 2,6-di-tert-butyl-4-methylphenol (0.6 mg, 0.0026 mmol), and tri-n-butyl isopropenyl stannane (644 mg, 1.95 mmol). The mixture was heated to 100–105° C. with continued stirring for 3 h. The mixture was allowed to cool to room temperature and diluted with ether (100 mL). This mixture was extracted by water twice, and 1,8-diazabicyclo[5.4.0]undec-7-ene (0.417 mL) was added and the mixture filtered through silica gel. The filtrate was dried and chromatographed to yield a colorless oil (420 mg, 91%).

Compound K: 20% Palladium hydroxide on carbon was added to a THF solution (5 mL) of compound J (benzyl 5-benzyloxy-2-isopropenylbenzoate). The suspension was stirred for 5 h. The solid was then removed by filtration. The filtrate was concentrated and the residue was purified by HPLC to yield a white solid (134 mg, 64%)

Compound L: 4-methylmorpholine (0.113 mL, 1.033 mmol) was added to a DMF (7 mL) solution of compound K (134 mg, 0.689 mmol), methionine methyl ester hydrochloride (207 mg, 1.033 mmol), 1-hydroxybenzotriazole hydrate (139 mg, 1.033 mmol), and 1-(3-dimethylaminopropyl)-3-ethylcarbodiimide hydrochloride (218 mg, 1.136 mmol). The mixture was stirred at room temperature for 12 hours, diluted with ethyl acetate and extracted with water twice. Drying and chromatography yielded a colorless oil (239 mg, 99%).

Compound M: Diethyl azodicarboxylate (0.168 mL, 1.07 mmol) was added to a THF (7 mL) solution of compound G (233 mg, 0.893 mmol), compound L (276 mg, 0.849 mmol),and triphenylphosphine (280 mg, 1.07 mmol). The mixture was stirred at room temperature for 3 days. The solvent was then evaporated under vacuum and the residue was dissolved in ethyl acetate and extracted by water. Drying and chromatography yielded a colorless oil (447 mg, 93%). This product was further purified on HPLC (296 mg, 61%).

If the final product is to be an acid instead of an ester, a hydrolysis step is inserted into the synthetic pathway as follows: Lithium hydroxide solution, 1 M, (0.350 mL, 0.35 mmol) was added to a dioxane (0.350 mL) solution of the appropriate ester (0.035 mmol). The mixture was stirred at room temperature for 1 h. A solution of 1 N hydrochloric acid was added to quench the reaction. The mixture was extracted by ethyl acetate. The ethyl acetate solution was extracted by brine and dried over sodium sulfate. Evaporation of the acetate yielded a colorless oil (20 mg, 100%).

Compound N: To a solution of compound M (278 mg, 0.489 mmol) in acetic acid (4 mL), DMF (0.4 mL), and $H_2O$ (0.2 mL) was added methoxycarbonylsulfenyl chloride (88.9 mL, 0.98 mmol) at 0° C. The solution was stirred for 1.5 h, during this period the solution was allowed to warm to the room temperature. The solution was concentrated under vacuum and to the residue was added triethylsilane (0.391 mL, 2.45 mmol) and trifluoroacetic acid (4.8 mL) at room temperature. The solution was stirred for 15 min. and concentrated under vacuum. The residue was purified by HPLC to yield a colorless oil (350 mg, >100%)

Compound 1: To a solution of compound 14 (350 mg, 0.489 mmol) in THF (4 mL) and $H_2O$ (0.4 mL) and trifluoroacetic acid (0.4 mL) was added a 1 M THF solution of trimethylphosphine (1.47 mL, 1.47 mmol) at room temperature. The solution was stirred at room temperature for 1 h. The solution was concentrated and the residue was dissolved in methanol and purified by HPLC. After evaporation of the HPLC eluent under vacuum, the residue was dissolved in $H_2O$ (120 mL) and acetonitrile (10 mL). The solution was freeze-dried to yield a white powder (229.6 mg, 87%).

$^1$H NMR (CD$_3$OD): d 8.76 (1H, d, J=7.7), 7.33 (1H, d, J=8.7), 7.02 (1H, dd, J=8.7, 2.7), 6.88 (1H, d, J=2.7), 4.73–4.78 (1H, m), 4.12–4.18 (2H, m), 3.77 (3H, s), 3.58–3.60 (1H, m), 3.19 (1H, sept., J=6.9), 2.94 (1H, dd, J=14.7, 4.9), 2.82 (1H, dd, J=14.7, 6.1), 2.53–2.68 (2H, m), 1.97–2.27 (4H, m), 2.10 (3H, s), 1.23 (3H, d, J=6.9), 1.20 (3H, d, J=6.9).

Example 2

Preparation of Compound 36

Compound NN: To a solution of compound M (397 mg, 0.699 mmol) in acetic acid (3 mL), DMF (0.3 mL), and H$_2$O (0.15 mL) was added methoxycarbonylsulfenyl chloride (107 mg, 0.84 mmol) at 0° C. The solution was stirred for 1.5 h, during this period it was allowed to warm to the room temperature. The solution was concentrated under vacuum, and the residue was diluted with ethyl acetate and extracted by aqueous sodium bicarbonate solution, water and brine. Drying and chromatography yielded a white solid (325 mg, 75%), Compound NN.

Compound XX: To a solution compound N (325 mg, 0.526 mmol) in aqueous THF (5 mL THF and 1 mL H2O) was added a 1.0 M THF solution of trimethylphosphine (1.1 mL, 1.1 mmol). The solution was stirred at room temperature for 30 minutes. A residue oil was obtained after the evaporation of solvent in vacuum.

To this residue was added methanol (1 ml), H$_2$O (0.5 mL), and NaHCO$_3$ (50 mg, 0.60 mmol). To this solution iodine (76 mg, 0.3 mmol) in methanol was added dropwise until a color persisted. The solution was diluted with water and was extracted with ethyl acetate. The organic extracts were washed with water and brine and dried over sodium sulfate. A white solid (289 mg) was obtained after removal of solvent in vacuum.

1.0 M Aqueous lithium hydroxide solution (5 mL, 5 mmol) was added to a dioxane (5 mL) solution containing the aforementioned solid (289 mg). The mixture was stirred at room temperature for 0.5 h. A solution of 1 N hydrochloric acid was added to quench the reaction. The mixture was extracted with ethyl acetate. Drying over sodium sulfate, filtration, and evaporation gave a residue (313 mg), Compound XX, which was used directly without further purification.

Compound YY: 4-methylmorpholine (82 mg, 0.81 mmol) was added to a DMF (5 mL) solution containing compound XX (313 mg), furfurylamine hydrochloride (109 mg, 0.81 mmol), 1-hydroxybenzotriazole hydrate (109 mg, 0.81 mmol), and 1-(3-dimethylaminopropyl)-3-ethylcarbodiimide hydrochloride (211 mg, 1.1 mmol). The mixture was stirred at room temperature for 12 hours, diluted with ethyl acetate, and washed with water twice. Drying and chromatography yielded a colorless oil (259 mg, 83%), Compound YY.

Compound 36: Trifluoroacetic acid (1 mL) was added to a mixture of Compound YY (259 mg, 0.438 mmol), triethylsilane (0.430 mL, 2.70 mmol) and dichloromethane (0.430 mL) at room temperature. The solution was stirred for 15 min. and concentrated under vacuum to obtain a residue.

The aforementioned residue was dissolved in THF (5 mL), H$_2$O (0.25 mL), and trifluoroacetic acid (0.25 mL). To this mixture was added a THF solution (1 M) of trimethylphosphine (1.6 mL, 1.6 mmol) at room temperature. The solution was stirred at room temperature for 1 h. The solution was concentrated, and the residue was dissolved in methanol and purified by RP HPLC. After evaporation of the HPLC eluent under vacuum, the residue was dissolved in H$_2$O and acetonitrile. The solution was freeze-dried to yield a white powder (146 mg, 55%), Compound 36.

Example 3

Preparation of Compound 35

Compound Z: Sodium borohydride (21 mg, 0.543 mmol) was added to a methanol solution (5 mL) of compound D (121 mg, 0.494 mmol) in one portion. The mixture was stirred at room temperature for 1 h. The methanol was then evaporated under vacuum, and the residue was dissolved in ethyl acetate and extracted by saturated aqueous ammonium chloride and brine. Drying and chromatography yielded a white solid (78 mg, 64%), Compound Z.

Compound P: N-Iodosuccinimide (19.317 g, 85.856 mmol) was added to a solution of 4-isopropylbenzaldehyde (9.77 g, 65.920 mmol) in CH$_2$Cl$_2$ (40 mL), and the suspension was cooled to 0° C. Trifluoromethanesulfonic acid (30 mL) was added via addition funnel dropwise over 10 minutes. After 2 hours, the reaction mixture was poured onto ice (200 mL), and the resulting mixture was diluted with CH$_2$Cl$_2$ (100 mL). The organic phase was separated, and the aqueous phase was extracted with CH$_2$Cl$_2$ (2×50 mL). The combined organic phases were washed with H$_2$O (100 mL), 1 N NaOH (100 mL), H$_2$O (100 mL), 0.25 N Na$_2$S$_2$O$_3$ (100 mL), H$_2$O (100 mL), and brine (100 mL), and dried over Na$_2$SO$_4$, filtered, and concentrated to give an amber liquid (17.402 g, 96%), Compound P. Distillation gave a colorless liquid (14.584 g, 81%, bp=110–117° C. @ ca. 380 mm Hg).

Compound Q: To a mixture of compound P (541 mg, 1.97 mmol), triethylamine (418 mg, 4.14 mmol), triphenylphosphine (77 mg, 0.296 mmol), ethanol (3.3 ml), and DMF (3.3 mL) was added palladium acetate (22 mg, 0.1 mmol). A stream of carbon monoxide was passed through the mixture while the mixture was stirred and heated to 100 C. for 14 h. The mixture was then cooled and diluted with ethyl acetate. The solution was then washed with water, 1 N HCl, and water. Drying and chromatography yielded an oil (404 mg, 93%), Compound Q.

Compound R: Sodium borohydride (13 mg, 0.353 mmol) was added to a methanol solution (3 mL) of Compound Q (74 mg, 0.336 mmol) in one portion. The mixture was stirred at room temperature for 0.5 h. The methanol was then evaporated under vacuum, and the residue was dissolved in ethyl acetate and washed with saturated aqueous ammonium chloride, water, and brine. Drying and chromatography yielded a colorless oil (59 mg, 80%), Compound R.

Compound S: Triphenylphosphine (139 mg, 0.532 mmol) was added to a solution of compound R (59 mg, 0.266 mmol), carbon tetrabromide (177 mg, 0.532 mmol) in dichloromethane (3 mL). The solution was stirred at room temperature for 14 hours. The mixture was diluted with ethyl acetate and washed with water. Drying and chromatography yielded a colorless oil (29 mg, 39%), Compound S.

Compound T: Sodium hydride (4 mg, 0.167 mmol) was added to a solution of compound Z (38 mg, 0.153 mmol) and compound S (29 mg, 0.102 mmol) in DMF (1.5 mL). The mixture was stirred at room temperature for 14 h. It was then diluted with ethyl acetate and washed with water and brine. Drying and chromatography yielded an oil (42 mg, 91%), Compound T.

Compound U: 1.0 M Aqueous lithium hydroxide solution (1.02 mL, 1.02 mmol) was added to a dioxane (1 ml) solution containing compound T (42 mg, 0.102 mmol). The mixture was stirred at 60° C. for 14 h and was then allowed to cool to room temperature. A solution of 1 N HCl was added to quench the reaction. The mixture was extracted with ethyl acetate. The ethyl acetate was washed with brine and dried over sodium sulfate. A residue was obtained after evaporation of solvent under vacuum. The residue was purified on RP HPLC to obtain an oil (26 mg, 67%), Compound U.

Compound V: 4-methylmorpholine (12.4 mg, 0.123 mmol) was added to a DMF (1 mL) solution containing V (26 mg, 0.062 mmol), methionine methyl ester hydrochloride (25 mg, 0.123 mmol), 1-hydroxybenzotriazole hydrate (17 mg, 0.123 mmol), and 1-(3-dimethylaminopropyl)-3-ethylcarbodiimide hydrochloride (30 mg, 0.154 mmol). The mixture was stirred at room temperature for 12 hours, diluted with ethyl acetate, and washed with water twice. Drying and chromatography yielded a colorless oil (29 mg, 83%), Compound V.

Compound 35: Compound 35 was prepared from compound V using procedures similar to those described for compound 36 from compound M.

Compounds 27 and 30: Compounds 27 and 30 were prepared from compound V in procedures similar to those used to prepare compounds 1 and 11 from compound M.

Biological Examples

Ras proteins mediate the transformation of normal cells to cancer cells in many human cancers. Before becoming membrane associated and fully functional, ras proteins require post-translational addition of a 15 to 20 carbon prenyl group. Compounds which inhibit prenylation will, therefore, inhibit the growth of ras-related cancers.

Compounds of the invention were screened in art accepted in vitro assays. First, each potential inhibitor compound was shown to inhibit FTase-mediated prenylation (Table 1). Second, each compound was shown to inhibit GGTase I-mediated prenylation (Table 1). Third, each compound was shown to inhibit ras protein post-translational processing in whole cells (Table 2). Clearly, the compounds of the invention inhibit the prenylating activity of FTase, GGTase I, or in most cases, both enzymes, with different potencies.

Thus, the ability of the compounds of the invention to inhibit protein processing has been demonstrated in two separate in vitro assays. The ability of the compounds of the invention to inhibit ras-related cancer growth has been demonstrated in an in vitro assay and one in vivo experiment. The compounds of the invention are effective inhibitors of ras-related cancers.

Example 2

In Vitro Inhibition of Prenyltransferases

The ability of the disclosed inhibitor compounds to inhibit FTase was measured according to a published prenylation assay (Moores et al., *J. Biol Chem.* 266:14603 (1991)). Recombinant FTase with 3 $\mu$M recombinant H-ras and 440 nM [$^3$H] farnesylpyrophosphate were used were used. The inhibitors were diluted in assay buffer, and each assay mixture was incubated 15 min. at 37° C. Where inhibition of GGTase I was measured, GGTase I with 5 $\mu$M recombinant, H-ras (61 L, CAIL) and 1 mM [$^3$H] geranylgeranyl diphosphate were used.

The $IC_{50}$ (concentration of compound needed to cause 50% inhibition of isoprenylation) values are presented in Table 1. Nanomolar concentrations of the indicated compounds were sufficient to inhibit farnesylation of ras proteins in vitro. For screening candidate compounds useful for the treatment of ras-associated tumors, the FTase assay is preferred. One embodiment of the invention selectively inhibits FTase. Substitutions which confer GGTase I specificity as taught herein also produced potent inhibitors of GGTase I.

TABLE 1

| Compound Number | $IC_{50}[\mu M]$ FTase | GGTase I |
|---|---|---|
| 2 | 0.045 | 1.9 |
| 3 | 0.50 | 1.7 |
| 4 | 0.030 | 1.9 |
| 5 | 6.3 | 40.0 |
| 6 | 1.3 | 4.2 |
| 7 | 0.093 | 3.0 |
| 8 | 0.89 | >100 |
| 9 | 0.022 | 3.8 |
| 10 | 0.030 | 2.5 |
| 11 | 0.021 | 0.39 |
| 12 | 0.004 | 0.038 |
| 13 | 0.004 | 0.032 |
| 14 | 0.015 | 0.13 |
| 30 | 0.015 | 0.93 |
| 31 | 0.35 | 8.9 |
| 32 | 0.47 | 100.0 |

Thus, compound of the invention assayed was shown to inhibit Ftase-meditated prenylation (Table 1). Each compound was also shown to inhibit GGTase-mediated prenylation (Table 1).

Example 3

Inhibition of Prenylation in Whole Cells

The ability of compounds of the invention to inhibit H-ras farnesylation was determined. H-ras (61 L) transformed NIH3T3 fibroblasts were generously provided by C. Der, Univ. N. Carolina. These fibroblasts were treated for 24 h with 50 $\mu$M lovastatin or vehicle control or the indicated concentrations of inhibitor. Lovastatin is an HMG-CoA reductase inhibitor. HMG-CoA reductase is an essential enzyme in the cellular synthesis of the prenyl groups with which ras proteins are modified. The cells were lysed in 1% NP-40, 5 mM Tris-HCl (pH 8.0), 5 mM EDTA, 0.1 mM N-tosyl-L-phenylalanine chloromethyl ketone, 0.1 mM N-tosyl-L-lysine chloromethyl ketone, and 1 mM phenylmethylsulfonyl fluoride. The lysate was centrifuged (15000×g, 5 min.) and the supernatant was used as a cell extract. Total protein was separated by SDS-PAGE in 15% acrylamide gel. Processed ras can be differentiated from non-processed ras by its mobility in polyacrylamide gels. After transfer to IMMOBILON P™ membrane (Millipore), the blots were probed with LA069 mouse monoclonal antibody to H-ras (Quality Biotech). All Western blots were developed using ECL chemiluminescent reagents (Amersham) and the relative amounts of farnesylated and non-farnesylated ras were quantitated using the inhibition obtained by 50 $\mu$M lovastatin as 100% reference.

The $IC_{50}$ values for inhibition H-ras prenylation are presented in Table 2. Sub-micromolar concentrations are sufficient to inhibit farnesylation of ras proteins in whole cells.

TABLE II

| Compound Number | $IC_{50} [\mu M]$ H-ras processing |
|---|---|
| 1 | 0.039 |
| 15 | 4.1 |
| 16 | >10 |
| 17 | 3.3 |

TABLE II-continued

| Compound Number | IC$_{50}$ [μM] H-ras processing |
|---|---|
| 18 | >50 |
| 19 | 46% @ 50 |
| 20 | 38% @ 50 |
| 21 | >50 |
| 22 | 0.122 |
| 23 | 31 |
| 24 | 0.298 |
| 25 | 3.1 |
| 26 | 3.2 |
| 27 | 0.049 |
| 28 | 42% @ 50 |
| 29 | >50 |

Sub-micromolar concentrations are sufficient to inhibit farnesylation of ras protein in whole cells. Clearly, the compounds of the invention inhibit the prenylating activity of FTase, GGTase, or in most cases, both enzymes. The compounds inhibit these enzymes with different potencies; preferred compounds of the invention inhibit FTase more potently than GGTase.

Thus, the ability of the compounds of the invention to inhibit protein modification by prenyltransferases has been demonstrated in two separate in vitro assays.

Example 4

Inhibition of Human Tumor Xenograft in Mice

H-ras (61 L) transformed NIH3T3 fibroblasts were grown in Dulbecco's modified Eagle's medium supplemented with 10% heat-inactivated calf serum. 100 U/mL penicillin, 100 μg/mL streptomycin, and 0.75 mg/mL G418 (GIBCO) and incubated at 37° C. in 5% CO$_2$. Cells were harvested from exponential-phase cultures with trypsin-EDTA, centrifuged at 160×g for 5 min, washed once with 10 mL cold Hank's balanced salt solution (HBSS, GIBCO), and resuspended at a concentration of 1×10$^6$ cells/mL.

Five week old female athymic nude mice were obtained from SLC (3371-8, Kotoummachi, Hamamatsu-shi, Shizuoka 431-11, Japan) and maintained under pathogen-free conditions. The mice were subcutaneously injected in the lateral flank with 1×10$^5$ H-ras transformed cells/mouse.

Inhibitor compound 1 was suspended in 5% glucose in a total injection volume of 0.2 mL. Three dosage concentrations were prepared, 100, 50 and 25 mg/kg. Compound 1 was intravenously injected daily in the tail vein for 5 consecutive days, starting the day after the implantation (day 0). The control group was injected with vehicle only. Body weight and tumor dimensions were measured at days 7, 10, and 14. Tumor volume was estimated by the following calculation: tumor volume=(0.5)(length×width×width). At day 14, each mouse was euthanized with CO$_2$(g), and each tumor was excised and weighed. The statistical significance was estimated by the Student's T-test. Tumor volumes are shown in FIG. 1.

What is claimed is:
1. A compound of the following formula

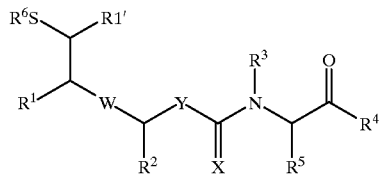

where
R$^1$ is hydroxy, hydrogen, C$_{1-8}$alkyl or NR$^7$R$^8$ wherein R$^7$ and R$^8$ are independently hydrogen, C$_{1-8}$ alkyl, C$_{1-8}$ acyl, C$_{2-14}$ alkyloxycarbonyl or when taken with R$^6$ forms a heterocyclic ring containing from 3 to 10 carbon atoms;

R$^{1'}$ is hydrogen, lower alkyl or lower aryl;

R$^2$ is hydrogen, C$_{1-8}$ alkyl, (C$_{6-40}$ aryl)(C$_{0-6}$ alkyl), or (C$_{3-10}$heteroaryl) (C$_{0-6}$ alkyl);

R$^3$ is hydrogen, C$_{1-6}$ alkyl, (C$_{6-20}$ aryl)(C$_{0-6}$ alkyl);

R$^4$ is hydroxy, C$_{1-6}$ alkoxy, or NR$^{11}$R$^{12}$ where R$^{11}$ and R$^{12}$ are independently hydrogen, C$_{1-8}$ alkyl, C$_{6-18}$aryl, C$_{4-18}$heteroaryl, C$_{1-8}$alkyl-C$_{6-18}$aryl or when taken together C$_{2-8}$heterocycloalky;

R$^5$ is the residue of a natural amino acid or is D—E—F where D is C$_{1-12}$ alkyl or C$_{2-12}$ alkenyl, E is oxygen, sulfur, nitrogen or null and F is hydrogen, C$_{1-10}$ alkyl, C$_{6-12}$aryl, CO$_2$R$^9$, NR$^9$R$^{10}$ or C(O)NR$^9$R$^{10}$ where R$^9$ and R$^{10}$ are independently hydrogen, C$_{1-8}$ alkyl or when taken together C$_{2-8}$heterocycloalkyl;

R$^6$ is hydrogen, C$_{1-8}$ alkyl, C$_{1-8}$ acyl or when taken together with R$^1$ forms a heterocyclic ring containing from 3 to 10 carbon atoms or is the moiety

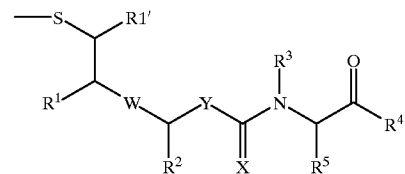

wherein
R$^1$, R$^{1'}$, R$^2$, R$^3$, R$^4$, R$^5$, W, X and Y are selected such that said compound is a disulfide bond-linked dimer;
W is C$_{0-8}$ alkyl, or C$_{2-8}$ alkenyl;
X is oxygen, sulfur or two hydrogen atoms;
Y is —M—O—P— where M is C$_{0-6}$ alkyl, O is oxygen-C$_{0-4}$ alkyl and P is C$_{6-20}$ aryl, optionally additionally mono- or polysubstituted with C$_{6-20}$ aryl, C$_{6-20}$ heteroaryl, C$_{1-18}$ alkyl, C$_{2-18}$ alkenyl, C$_{2-18}$ alkynyl, C$_{1-18}$ alkoxy, C$_{1-18}$ alkylthio, C$_{6-20}$ aryloxy, amino, hydroxy, or halogen;

and pharmaceutically acceptable salts thereof.

2. A compound of claim 1 where
R$^1$ is NR$^7$R$^8$ wherein R$^7$ and R$^8$ are independently hydrogen or C$_{1-8}$ alkyl;
R$^{1'}$ is hydrogen or C$_{1-5}$ alkyl;
R$^2$ is hydrogen or C$_{1-8}$ alkyl;
R$^3$ is hydrogen or C$_{1-6}$ alkyl;
R$^4$ is hydroxy or C$_{1-6}$ alkoxy;
R$^5$ is D—E—F where D is C$_{1-12}$ alkyl or C$_{2-12}$ alkenyl, E is oxygen, sulfur, or null and F is hydrogen, C$_{1-10}$ alkyl, $N^R9R^{10}$ or $C(O)NR^9R^{10}$ where $R^9$ and $R^{10}$ are independently hydrogen, $C_{1-8}$ alkyl or when taken together $C_{2-8}$ heterocycloalkyl;

$R^6$ is hydrogen, $C_{1-8}$ alkyl, $C_{1-8}$ acyl or when taken together with $R^1$ forms a heterocyclic ring containing from 3 to 10 carbon atoms or is the moiety

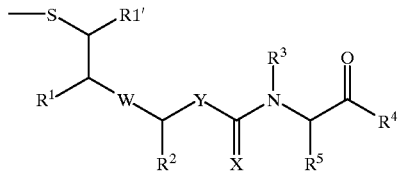

wherein
$R^1$, $R^{1'}$, $R^2$, $R^3$, $R^4$, $R^5$, W, X and Y are selected such that said compound is a disulfide bond-linked dimer;
W is $C_{0-8}$ alkyl, or $C_{2-8}$ alkenyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

3. A compound of claim 1 where
$R^1$ is $NR^7R^8$ wherein $R^7$ and $R^8$ are independently hydrogen or $C_{1-8}$ alkyl;
$R^{1'}$ is hydrogen or $C_{1-3}$ alkyl;
$R^2$ is hydrogen or $C_{1-8}$ alkyl;
$R^3$ is hydrogen or $C_{1-6}$ alkyl;
$R^4$ is hydroxy or $C_{1-6}$ alkoxy;
$R^5$ is D—E—F where D is $C_{1-12}$ alkyl or $C_{2-12}$ alkenyl, E is sulfur or oxygen and F is hydrogen, $C_{1-10}$ alkyl or $NR^9R^{10}$ where $R^9$ and $R^{10}$ are independently hydrogen, $C_{1-8}$ alkyl or when taken together $C_{2-8}$ heterocycloalkyl;
$R^6$ is hydrogen, $C_{1-8}$ alkyl, $C_{1-8}$ acyl or when taken together with $R^1$ forms a heterocyclic ring containing from 3 to 10 carbon atoms;
W is $C_{0-8}$ alkyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

4. A compound of claim 1 where
$R^1$ is $NR^7R^8$ wherein $R^7$ and $R^8$ are hydrogen;
$R^{1'}$ is hydrogen or methyl;
$R^2$ is hydrogen or $C_{1-6}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is hydrogen or $C_{1-6}$ alkyl;
$R^6$ is hydrogen;
W is $C_{0-3}$ alkyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

5. A compound of claim 1 where
$R^1$ is $NR^7R^8$ wherein $R^7$ and $R^8$ are hydrogen;
$R^2$ is hydrogen or $C_{1-4}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is hydrogen or $C_{1-3}$ alkyl;
$R^6$ is hydrogen;
W is $C_{0-3}$ alkyl;
X is oxygen or two hydrogen atoms;
Y is —M—O—P— where M is $C_{0-6}$ alkyl, O is oxygen-$C_{0-4}$ alkyl and P is $C_{6-20}$ aryl, optionally additionally mono- or polysubstituted with $C_{6-20}$ aryl, $C_{6-20}$ heteroaryl, $C_{1-18}$ alkyl, $C_{2-18}$ alkenyl, $C_{2-18}$ alkynyl, $C_{1-18}$ alkoxy, $C_{1-18}$ alkylthio, $C_{6-20}$ aryloxy, amino, hydroxy, or halogen;
and pharmaceutically acceptable salts thereof.

6. A compound of claim 1 where
$R^1$ is $NR^7R^8$ wherein $R^7$ and $R^8$ are hydrogen;
$R^2$ is hydrogen or $C_{1-4}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is $C_{1-3}$ alkyl;
$R^6$ is hydrogen;
W is $C_{0-3}$ alkyl;
X is oxygen;
Y is —M—O—P— where M is $C_{0-6}$ alkyl, O is oxygen-$C_{0-4}$ alkyl and P is $C_{6-12}$ aryl, optionally additionally mono- or polysubstituted with $C_{6-12}$ aryl, $C_{6-12}$ heteroaryl, $C_{1-6}$ alkyl, $C_{2-6}$ alkenyl, $C_{1-18}$ alkoxy, $C_{1-6}$ alkylthio, $C_{6-12}$ aryloxy, amino, hydroxy, or halogen;
and pharmaceutically acceptable salts thereof.

7. A compound of claim 1 where
$R^1$ is $NR^7R^8$ wherein $R^7$ and $R^8$ are hydrogen;
$R^2$ is hydrogen or $C_{1-4}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is $C_{1-3}$ alkyl;
$R^6$ is hydrogen;
W is $C_{0-3}$ alkyl;
X is oxygen;
Y is —M—O—P— where M is $C_{0-6}$ alkyl, O is oxygen and P is $C_{6-12}$ aryl, optionally additionally mono- or polysubstituted with $C_{6-12}$ aryl, $C_{6-12}$ heteroaryl, $C_{1-6}$ alkyl, $C_{2-6}$ alkenyl, $C_{1-18}$ alkoxy, $C_{1-6}$ alkylthio, $C_{6-12}$ aryloxy, amino, hydroxy, or halogen;
and pharmaceutically acceptable salts thereof.

8. A compound of claim 1 where
$R^1$ is $NR^7R^8$ wherein $R^7$ and $R^8$ are hydrogen;
$R^2$ is hydrogen or $C_{1-4}$ alkyl;
$R^3$ is hydrogen or $C_{1-3}$ alkyl;
$R^4$ is hydroxy or $C_{1-3}$ alkoxy;
$R^5$ is D—E—F where D is $C_{1-6}$ alkyl, E is sulfur and F is $C_{1-3}$ alkyl;

R⁶ is hydrogen;
W is $C_{0-3}$ alkyl;
X is oxygen;
Y is —M—O—P— where M is $C_{0-6}$ alkyl, O is $C_{0-4}$ alkyl and P is $C_{6-12}$ aryl, optionally additionally mono- or polysubstituted with $C_{6-12}$ aryl, $C_{6-12}$ heteroaryl, $C_{1-6}$ alkyl, $C_{2-6}$ alkenyl, $C_{1-18}$ alkoxy, $C_{1-6}$ alkylthio, $C_{6-12}$ aryloxy, amino, hydroxy, or halogen;
and pharmaceutically acceptable salts thereof.

9. A compound of claim 1 where
$R^1$ is $NR^7R^8$ wherein $R^7$ and $R^8$ are hydrogen;
$R^2$ is hydrogen;
$R^3$ is hydrogen;
$R^4$ is hydroxy;
$R^5$ is D—E—F where D is ethyl, E is sulfur and F is methyl;
$R^6$ is hydrogen;
W is methyl;
X is oxygen;

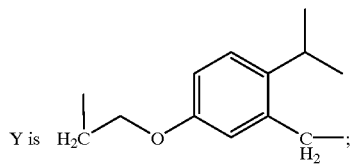

and pharmaceutically acceptable salts thereof.

10. A compound of claim 1 where $R^1$ is $NR^7R^8$ wherein $R^7$ and $R^8$ are hydrogen;
$R^2$ is hydrogen;
$R^3$ is hydrogen;
$R^4$ is methoxy;
$R^5$ is D—E—F where D is ethyl, E is sulfur and F is methyl;
$R^6$ is hydrogen;
W is methyl;
X is oxygen;

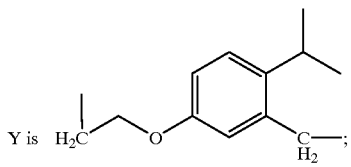

and pharmaceutically acceptable salts thereof.

* * * * *